(12) United States Patent
Kobayashi et al.

(10) Patent No.: US 11,918,712 B2
(45) Date of Patent: Mar. 5, 2024

(54) BACTERIA TREATMENT MECHANISM AND BACTERIA TREATMENT METHOD

(71) Applicant: JGC JAPAN CORPORATION, Kanagawa (JP)

(72) Inventors: Takeshi Kobayashi, Kanagawa (JP); Takeshi Kojima, Kanagawa (JP)

(73) Assignee: JGC JAPAN CORPORATION, Kanagawa (JP)

( * ) Notice: Subject to any disclaimer, the term of this patent is extended or adjusted under 35 U.S.C. 154(b) by 818 days.

(21) Appl. No.: 16/975,707

(22) PCT Filed: May 10, 2019

(86) PCT No.: PCT/JP2019/018690
§ 371 (c)(1),
(2) Date: Aug. 25, 2020

(87) PCT Pub. No.: WO2019/244501
PCT Pub. Date: Dec. 26, 2019

(65) Prior Publication Data
US 2020/0390929 A1    Dec. 17, 2020

(30) Foreign Application Priority Data

Jun. 20, 2018 (JP) ................................ 2018-116967

(51) Int. Cl.
*A61L 2/08* (2006.01)
*A61L 2/26* (2006.01)
(Continued)

(52) U.S. Cl.
CPC ................ *A61L 9/14* (2013.01); *A61L 2/082* (2013.01); *A61L 2/087* (2013.01); *A61L 2/26* (2013.01);
(Continued)

(58) Field of Classification Search
CPC . A61L 2/082; A61L 2/087; A61L 2/26; A61L 9/14
See application file for complete search history.

(56) References Cited

U.S. PATENT DOCUMENTS

2009/0047174 A1\* 2/2009 Hill ......................... A61L 2/208
422/111
2010/0189607 A1\* 7/2010 Yokoi ....................... A61L 2/22
422/600

(Continued)

FOREIGN PATENT DOCUMENTS

CN    101417719    4/2009
CN    101612522    12/2009
(Continued)

OTHER PUBLICATIONS

"Office Action of China Counterpart Application" with English translation thereof, dated Sep. 14, 2022, p. 1-p. 12.
(Continued)

*Primary Examiner* — Timothy C Cleveland
(74) *Attorney, Agent, or Firm* — JCIPRNET

(57) ABSTRACT

A bacteria treatment mechanism and a bacteria treatment method capable of reliably sterilizing an exterior of an article are provided.
A bacteria treatment mechanism includes: a bacteria treatment unit that has a space for performing bacteria treatment; a radiation irradiation unit that irradiates the bacteria treatment unit with radiation for performing the bacteria treatment; an air supply duct that supplies air to the bacteria treatment unit; a decontamination treatment fluid supply unit that supplies a decontamination treatment fluid to the air supply duct during initial decontamination of the air supply duct; and an exhaust duct that exhausts molecules in the bacteria treatment unit.

16 Claims, 2 Drawing Sheets

Figure 1:
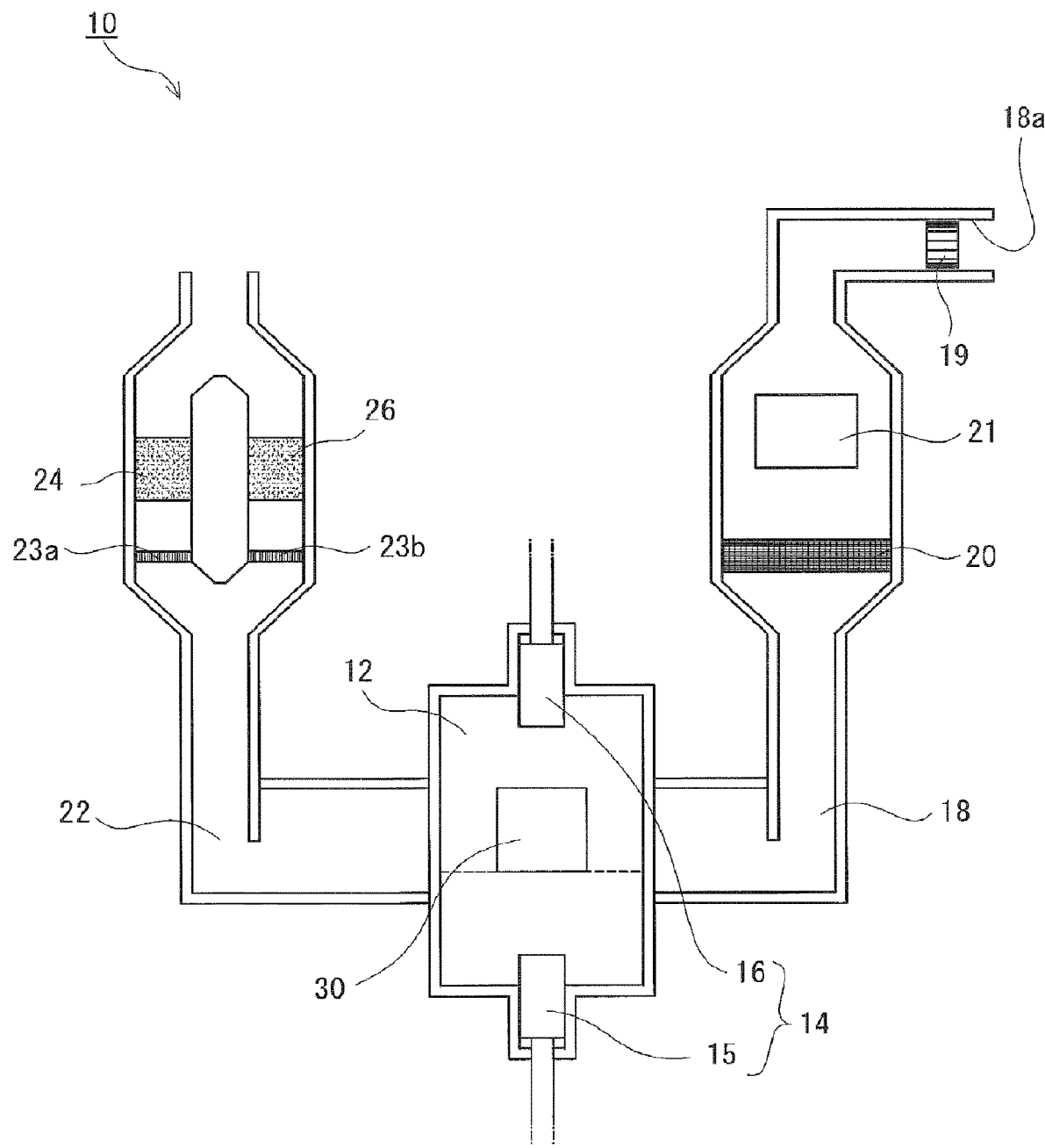

(51) Int. Cl.
   *A61L 9/14*   (2006.01)
   *B01D 53/86*  (2006.01)
   *B01D 53/88*  (2006.01)
(52) U.S. Cl.
   CPC ....... *B01D 53/8675* (2013.01); *B01D 53/885* (2013.01); *A61L 2202/11* (2013.01); *A61L 2202/122* (2013.01); *A61L 2202/13* (2013.01); *A61L 2202/23* (2013.01); *B01D 2257/106* (2013.01)

(56) References Cited

U.S. PATENT DOCUMENTS

| | | | | |
|---|---|---|---|---|
| 2012/0275967 | A1* | 11/2012 | Yokoi | A61L 9/14 422/291 |
| 2015/0108366 | A1* | 4/2015 | Kawasaki | A61L 2/087 250/453.11 |
| 2018/0344884 | A1* | 12/2018 | Kawasaki | B65B 55/08 |

FOREIGN PATENT DOCUMENTS

| | | |
|---|---|---|
| CN | 101720233 | 6/2010 |
| CN | 105039932 | 11/2015 |
| CN | 107614021 | 1/2018 |
| CN | 213311939 | 6/2021 |
| EP | 2578239 | 4/2013 |
| JP | 2012024385 | 2/2012 |
| JP | 2015039684 | 3/2015 |
| JP | 2016220747 | 12/2016 |
| WO | 03068272 | 8/2003 |
| WO | 2011148833 | 12/2011 |
| WO | 2016190088 | 12/2016 |

OTHER PUBLICATIONS

"Office Action of China Counterpart Application" with English translation thereof, dated Oct. 10, 2022, p. 1-p. 17.

"International Search Report (Form PCT/ISA/210) of PCT/JP2019/018690," dated Aug. 6, 2019, with English translation thereof, pp. 1-4.

Didier Morisseau, et al., "SterStar system: continuous sterile transfer by e-beam," Radiation Physics and Chemistry, vol. 71, Sep. 2004, pp. 553-556.

"Office Action of China Counterpart Application" with English translation thereof, dated May 16, 2022, p. 1-p. 21.

* cited by examiner

BACTERIA TREATMENT MECHANISM AND BACTERIA TREATMENT METHOD

CROSS-REFERENCE TO RELATED APPLICATION

This application is a 371 application of international PCT application serial no. PCT/JP2019/018690, filed on May 10, 2019, which claims the priority benefit of Japan application no. 2018-116967, filed on Jun. 20, 2018. The entirety of each of the above-mentioned patent applications is hereby incorporated by reference herein and made a part of this specification.

TECHNICAL FIELD

The present invention relates to a bacteria treatment mechanism that irradiates an object with radiation to perform bacteria treatment, and a bacteria treatment method using the bacteria treatment mechanism.

BACKGROUND ART

Conventionally, in order to prevent mixture of bacteria or contamination in a sterile control area when bringing articles from a general control area in which a sterile control is not performed to the sterile control area such as a sterile isolator or a clean room, an apparatus for performing exterior sterilization of the articles is known (for example, see Patent Literature 1). In such an apparatus, the articles arranged in an electron beam irradiation area are irradiated with an electron beam from above and below to sterilize the articles.

Here, in the electron beam irradiation area, ozone ($O_3$) is generated by oxygen ($O_2$) in the air being irradiated with the electron beam. Since this ozone is harmful and needs to be removed from the electron beam irradiation area, an air supply duct and an exhaust duct are connected to the electron beam irradiation area to ventilate the electron beam irradiation area.

CITATION LIST

Patent Literature

Patent Literature 1: WO 03/068272 A

SUMMARY OF INVENTION

Technical Problem

By the way, in the above-mentioned apparatus, although the electron beam irradiation area is sterilized, there is a problem in that the inside of the air supply duct or the exhaust duct is out of the electron beam irradiation area, so that bacteria treatment is not performed. In particular, if the bacteria in the air supply duct are not treated, there is a risk that contaminated air is supplied to the electron beam irradiation area, and the sterilized articles arranged in the electron beam irradiation area are re-contaminated.

The present invention provides a bacteria treatment mechanism and a bacteria treatment method capable of reliably sterilizing an exterior of an article.

Solution to Problem

According to the present invention, a bacteria treatment mechanism includes:

a bacteria treatment unit that has a space for performing bacteria treatment;
a radiation irradiation unit that irradiates the bacteria treatment unit with radiation for performing the bacteria treatment;
an air supply duct that supplies air to the bacteria treatment unit;
a decontamination treatment fluid supply unit that supplies a decontamination treatment fluid to the air supply duct during initial decontamination of the air supply duct; and
an exhaust duct that exhausts molecules in the bacteria treatment unit.

If such configurations are provided, by preliminarily performing initial decontamination for the inside of the air supply duct with the decontamination treatment fluid, air contaminated with bacteria is not introduced into the bacteria treatment unit, recontamination of the sterilized article (object) can be prevented, and the exterior of the article (object) can be reliably sterilized.

In addition, in the bacteria treatment mechanism according to the present invention,
the decontamination treatment fluid may be a gas or mist having a decontamination function.

That is, as the decontamination treatment fluid, a gas, a mist-like liquid, or the like having a decontamination function is used.

In addition, in the bacteria treatment mechanism according to the present invention,
the decontamination treatment fluid may contain hydrogen peroxide.

For example, specific examples of the decontamination treatment fluid include hydrogen peroxide and hydrogen peroxide solution.

In addition, in the bacteria treatment mechanism according to the present invention,
in the bacteria treatment unit, an object may be sterilized by the radiation emitted from the radiation irradiation unit.

That is, the electron beam is used to perform sterilization.

In addition, in the bacteria treatment mechanism according to the present invention,
the object may be a housing that accommodates an accommodated object therein and is formed of a shielding material that shields the radiation and secondary radiation that has a higher transparency than the radiation and is secondarily generated by the radiation,
an exterior of the housing may be sterilized by the radiation, and
the radiation and the secondary radiation may not penetrate through the accommodated object.

As a result, in a bacteria treatment process, only the exterior of the housing can be sterilized while protecting the accommodated object from the secondary radiation.

In addition, in the bacteria treatment mechanism according to the present invention,
the object may be configured to wrap an accommodated object covered with a shielding material that shields the radiation and secondary radiation that has a higher transparency than the radiation and is secondarily generated by the radiation, with a sterile maintaining material that maintains the inside in a sterile state,
an exterior of the sterile maintaining material may be sterilized by the radiation, and
the radiation and the secondary radiation may not penetrate through the accommodated object.

As a result, in the bacteria treatment process, only the exterior of the sterile maintaining material can be sterilized while protecting the accommodated object from the secondary radiation.

In addition, in the bacteria treatment mechanism according to the present invention, the object may be a container that accommodates an accommodated object therein and is formed by providing a layer made of a shielding material that shields the radiation and secondary radiation that has a higher transparency than the radiation and is secondarily generated by the radiation inside a structure, an exterior of the container may be sterilized by the radiation, and the radiation and the secondary radiation may not penetrate through the accommodated object.

As a result, in the bacteria treatment process, only the exterior of the container can be sterilized while protecting the accommodated object from the secondary radiation.

In addition, in the bacteria treatment mechanism according to the present invention, the radiation may be an electron beam and the secondary radiation may be an X-ray.

That is, an electron beam is mainly used as the radiation, and when the radiation is irradiated, X-ray having high transparency is secondarily generated.

In addition, in the bacteria treatment mechanism according to the present invention, a catalyst that decomposes molecules exhausted from the exhaust duct may be provided.

In this way, since the molecules used in the initial decontamination and the molecules generated in the bacteria treatment unit are decomposed by the catalyst and exhausted, the air in the surrounding environment can be prevented from being contaminated.

In addition, in the bacteria treatment mechanism according to the present invention, the catalyst may include one of a first catalyst that decomposes hydrogen peroxide and a second catalyst that decomposes ozone.

That is, as the molecules exhausted from the exhaust duct, hydrogen peroxide used in the initial decontamination and ozone generated in the pass box are assumed. By decomposing hydrogen peroxide and ozone with the catalyst, the air in the surrounding environment can be prevented from being contaminated.

In addition, in the bacteria treatment mechanism according to the present invention, an exhaust switching mechanism that guides the molecules exhausted to the exhaust duct to either the first catalyst or the second catalyst may be provided.

As such an exhaust switching mechanism, for example, a damper or the like can be considered.

In addition, in the bacteria treatment mechanism according to the present invention, the catalyst may decompose both hydrogen peroxide and ozone.

In this way, by combining the catalysts into one, the bacteria treatment mechanism can be downsized.

In addition, in the bacteria treatment mechanism according to the present invention, the bacteria treatment unit may be a pass box.

That is, it is preferable to use the pass box as the bacteria treatment unit.

According to the present invention, a bacteria treatment method includes:

an initial decontamination process of supplying a decontamination treatment fluid to an air supply duct during initial decontamination of the air supply duct;

an initial air supply process of supplying air to a bacteria treatment unit via the air supply duct;

an initial decomposition process of decomposing a fluid containing the decontamination treatment fluid exhausted from the bacteria treatment unit with a catalyst and releasing the fluid to the outside air;

a bacteria treatment process of irradiating the bacteria treatment unit with radiation to perform bacteria treatment of an object;

an aeration process of supplying air to the bacteria treatment unit through the air supply duct after the bacteria treatment, and exhausting the fluid in the bacteria treatment unit;

a decomposition process of decomposing the fluid in the bacteria treatment unit exhausted from the bacteria treatment unit with the catalyst or another catalyst and releasing the fluid to the outside air; and a take-out process of taking-out the object from the bacteria treatment unit after the decomposition process.

Through such processes, by preliminarily performing initial decontamination for the inside of the air supply duct with the decontamination treatment fluid, air contaminated with bacteria is not introduced into the bacteria treatment unit, recontamination of the sterilized object can be prevented, and the exterior of the object can be reliably sterilized. In addition, since the molecules used in the initial decontamination and the molecules generated in the bacteria treatment unit are decomposed by the catalyst and exhausted, the air in the surrounding environment can be prevented from being contaminated.

Advantageous Effects of Invention

According to the present invention, the present invention can provide the bacteria treatment mechanism and the bacteria treatment method capable of reliably sterilizing the exterior of the article.

BRIEF DESCRIPTION OF DRAWINGS

FIG. 1 is a schematic view illustrating a bacteria treatment mechanism according to an embodiment.

FIG. 2 is a view illustrating a pattern of an article including an accommodated object in the bacteria treatment mechanism according to the embodiment.

DESCRIPTION OF EMBODIMENTS

Hereinafter, a bacteria treatment mechanism according to an embodiment of the present invention will be described with reference to the drawings. Note that in the present specification, "sterilization" means that the sterility assurance level (SAL) is less than 10-6. In addition, "decontamination" means that the sterility assurance level (SAL) is less than 10−3. In addition, "bacteria treatment" is meant to include the sterilization and the decontamination.

FIG. 1 is a schematic view of a bacteria treatment mechanism according to an embodiment. As illustrated in FIG. 1, a bacteria treatment mechanism 10 includes a pass box 12, which is a bacteria treatment unit, an electron beam irradiator 14, which is a radiation irradiation unit, an air supply duct 18, a hydrogen peroxide generator 21, which is a decontamination treatment fluid supply unit, an exhaust duct 22, a first catalyst 24, and a second catalyst 26.

Here, the pass box 12 is a box-shaped apparatus having a space for accommodating an article 30 to be sterilized and having a double door (not illustrated) (a general control area side door and a sterile control area side door) used when the article 30 is taken in and out of a sterile control area. The pass box 12 preferably has a structure in which two doors are not opened at the same time, and has an air lock function for blocking the outside air from the sterile control area.

The electron beam irradiator 14 is an apparatus that irradiates the article 30 with an electron beam for sterilizing the article 30. The electron beam irradiator 14 includes a lower irradiator 15 that irradiates the article 30 with the electron beam from below, and an upper irradiator 16 that irradiates the article 30 with the electron beam from above. In this way, by irradiating the article 30 with the electron beam, an exterior of the article 30 is sterilized in a short time. Note that as the electron beam irradiator 14, only one of the lower irradiator 15 and the upper irradiator 16 may be provided.

Here, in the present embodiment, the electron beam is used as the radiation for performing the bacteria treatment, but the radiation is not limited thereto, and for example, X-rays or gamma rays can be used.

The air supply duct 18 and the exhaust duct 22 are pipes for achieving ventilation in the pass box 12, and are connected to surfaces on which the general control area side door and the sterile control area side door are formed, and left and right surfaces which do not correspond to the surface where the electron beam irradiator 14 is present.

The hydrogen peroxide generator 21 is an apparatus that generates hydrogen peroxide for initial decontamination in the air supply duct 18.

Note that in the present embodiment, for the initial decontamination in the air supply duct 18, the hydrogen peroxide is introduced into the air supply duct 18 as a decontamination treatment fluid, but the decontamination treatment fluid is not limited thereto, and for example, a gas such as an ethylene oxide gas, a formaldehyde gas, nitrogen dioxide, and methanol may be used, and a liquid such as a hydrogen peroxide solution or a peracetic acid solution may be made into a mist and introduced into the air supply duct.

An air supply fan 19 is provided at an air supply port 18a of the air supply duct 18, air is sent from the air supply duct 18 into the pass box 12 by the air supply fan 19, and the pass box 12 is ventilated.

In addition, the air supply duct 18 is preferably provided with an air filter 20 so as to remove dust and dirt contained in the air to be supplied into the pass box 12 and the decontamination treatment fluid. As such an air filter 20, for example, a high efficiency particulate air (HEPA) filter, an ultra low penetration air (ULPA) filter, or the like can be used.

The second catalyst 26 is a catalyst that decomposes ozone generated when oxygen in the air in the pass box 12 is irradiated with the electron beam and converts the ozone into oxygen. The first catalyst 24 is a catalyst that decomposes hydrogen peroxide introduced into the air supply duct 18 into oxygen and water.

The first catalyst 24 in the present embodiment is not particularly limited as long as it is a catalyst capable of detoxifying hydrogen peroxide, for example, "NHO-453" manufactured by JGC Universal Co., Ltd. and the like can be used.

In addition, the second catalyst 26 in the present embodiment is not particularly limited as long as it is a catalyst capable of detoxifying ozone, for example, "NHC-M" and "NHC-R" manufactured by JGC Universal Co., Ltd. can be used.

Note that in the present embodiment, since hydrogen peroxide at the time of initial decontamination and ozone at the time of electron beam irradiation are exhausted, the first catalyst 24 and the second catalyst 26 that decompose hydrogen peroxide and ozone are used, but for example, when an ethylene oxide gas, a formaldehyde gas, or the like is used instead of hydrogen peroxide at the time of initial decontamination, the ethylene oxide gas, the formaldehyde gas, or the like may be used as a detoxifying catalyst.

In addition, in the present embodiment, hydrogen peroxide is treated by the first catalyst 24 and ozone is treated by the second catalyst 26, but for example, like a catalyst described in U.S. Pat. No. 6,180,235, by using a catalyst capable of decomposing both ozone and hydrogen peroxide, it is possible to downside the bacteria treatment mechanism 10 by combining the catalysts into one.

The exhaust duct 22 is provided with dampers 23a and 23b as an exhaust switching mechanism, and the opening and closing of the dampers 23a and 23b can be switched so that during initial decontamination, that is, when hydrogen peroxide (molecules) is exhausted from the pass box 12 to the exhaust duct 22, the damper 23a is opened so that the exhaust gas is guided to the first catalyst 24, and in addition, during sterilization by electron beam irradiation, that is, when ozone (molecules) is exhausted from the pass box 12 to the exhaust duct 22, the damper 23b is opened so that the exhaust gas is guided to the second catalyst 26.

Next, a series of treatments of the bacteria treatment mechanism 10 will be described. First, in an initial state, hydrogen peroxide is generated by the hydrogen peroxide generator 21 and introduced into the air supply duct 18. When the hydrogen peroxide is introduced into the air supply duct 18, the inside of the air supply duct 18 is decontaminated by the hydrogen peroxide (initial decontamination process). In this way, by preliminarily decontaminating the inside of the air supply duct 18 in the initial state, uncontaminated air can be sent into the pass box 12 during ventilation.

Next, the air supply fan 19 supplies air through the air supply duct 18 (initial air supply process). The air and hydrogen peroxide in the air supply duct 18 and the pass box 12 are guided to the catalyst via the exhaust duct 22 (initial decomposition process). Here, the hydrogen peroxide is decomposed by the first catalyst 24 and then released to the outside air.

Once the initial decontamination is complete, the article 30 can be sterilized. When sterilizing the article 30, first, the general control area side door is opened and the article 30 is carried into the pass box 12. Next, when the general control area side door is closed, electron beams are emitted from the upper irradiator 16 and the lower irradiator 15, and the article 30 is irradiated with the electron beams from both upper and lower sides. As a result, the exterior of the article 30 is sterilized (bacteria treatment process). Note that when the article 30 is irradiated with the electron beam, oxygen ($O_2$) in the air existing in an irradiation area in the pass box 12 is irradiated with the electron beam, so that ozone ($O_3$) is generated.

After the sterilization treatment, air is supplied into the pass box 12 via the air supply duct 18 by an air supply unit (not illustrated), and the air in the pass box 12 and ozone are exhausted to the exhaust duct 22 (aeration process). Ozone is decomposed by the second catalyst 26 and then released to the outside air (decomposition process). Thereafter, the sterile control area side door is opened, and the sterilized article 30 is taken out from the pass box 12 (take-out process).

Note that in order to prevent recontamination, it is preferable to sterilize the article 30 after completion of the initial decontamination and continuously supply the air through the air supply duct 18 until the sterilized article 30 is taken out from the pass box 12.

According to the bacteria treatment mechanism 10 of the present embodiment, by preliminarily performing initial decontamination for the inside of the air supply duct 18 with hydrogen peroxide, air contaminated with bacteria is not introduced into the pass box 12, recontamination of the sterilized article 30 can be prevented, and the exterior of the article 30 can be reliably sterilized. In addition, since hydrogen peroxide used in the initial decontamination and ozone generated in the pass box 12 are decomposed by the catalysts and exhausted, it is possible to prevent air in the surrounding environment from being contaminated.

Note that when the article 30 is irradiated with the electron beam, X-rays (secondary radiation) may be secondarily generated. In this case, since a transparency of the X-rays is higher than that of the electron beam, it is necessary to consider the influence of X-rays. Hereinafter, this will be described step by step.

First, when the article 30 is not affected by either the electron beam or X-rays, the exterior of the article 30 is sterilized by the electron beam in the bacteria treatment process by irradiating the article 30 with the electron beam as described above. Here, as the article 30, small jigs such as a spoon may be considered.

In addition, when the article 30 includes contents affected by either the electron beam or the X-rays, various modes are conceivable for the article 30 in the above-described embodiment. For example, as an example of the case where the content of the article 30 is not affected by the X-rays but is affected by the electron beam, the article 30 is assumed to be one in which the content is covered with a resin container or a plastic bag. In this case, the electron beam can be shielded by the resin container or the plastic bag, and the electron beam can be prevented from penetrating the content. Note that in the bacteria treatment process, an exterior of the resin container or the plastic bag is sterilized by the electron beam.

Figure 2:
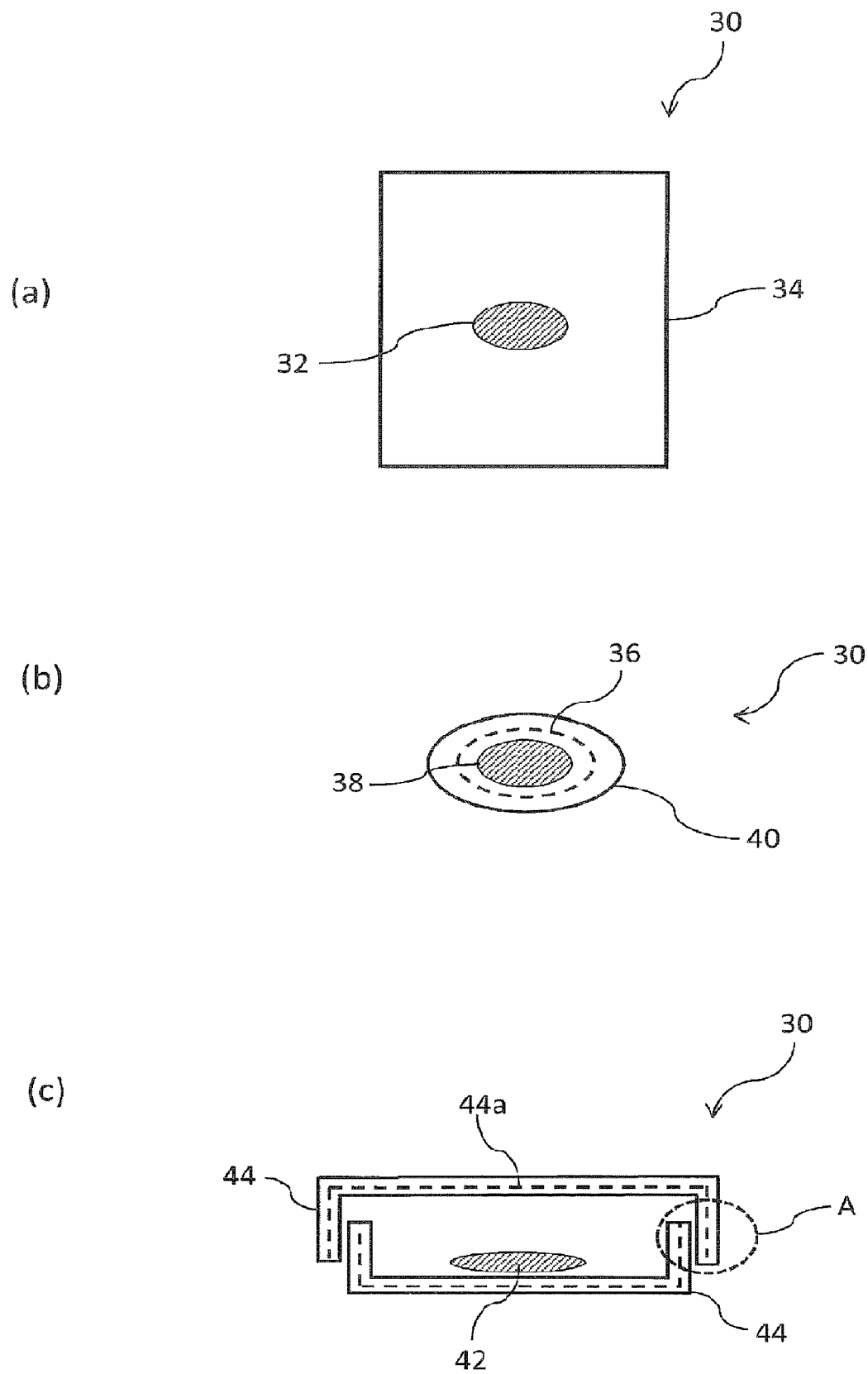

In addition, as an example of the case where the content of the article 30 is affected by both the electron beam and the X-rays, the cases illustrated in each of FIG. 2 are assumed as follows. For example, as illustrated in (a) of FIG. 2, the article 30 may be a housing 34 that accommodates an accommodated object 32 therein. Here, the housing 34 has a function of maintaining sterility, and a space inside the housing 34 is maintained in a sterile state. In addition, the housing 34 is formed of a shielding material such as lead that shields the electron beam and the X-rays. Therefore, in the bacteria treatment process, only an exterior of the housing 34 is sterilized, and the penetration of the electron beam and the X-rays into the accommodated object 32 is prevented. Note that as a specific example of the accommodated object 32, for example, a pipetter or the like can be considered.

In addition, as illustrated in (b) of FIG. 2, the article 30 may be one in which an accommodated object 38 covered with a shielding material 36 is wrapped with a sterile maintaining material 40. Note that the inside of the sterile maintaining material 40 is maintained in a sterile state. Here, when the article 30 is irradiated with the electron beam, the electron beam is shielded by the sterile maintaining material 40, but the secondarily generated X-rays penetrate through the sterile maintaining material 40. However, the X-rays that have penetrated through the sterile maintaining material 40 are shielded by the shielding material 36. Therefore, in the bacteria treatment process, only an exterior of the sterile maintaining material 40 is sterilized, and the penetration of the X-rays into the accommodated object 38 is prevented. Note that an electron beam having a high velocity may penetrate through the sterile maintaining material 40, but in this case also, the electron beam is shielded by the shielding material 36. In addition, as the sterile maintaining material 40, for example, a material capable of maintaining the sterile state, such as a plastic bag or a Tyvek sheet (registered trademark) is considered, and as the shielding material 36, a sheet using lead is considered.

In addition, as illustrated in (c) of FIG. 2, the article 30 may be a container 44 that accommodates an accommodated object 42 therein. Here, the container 44 is made of a composite material in which a layer made of a shielding material 44a is provided in a structure, and has a function of shielding the electron beam and the X-rays. Therefore, in the bacteria treatment process, only an exterior of the container 44 is sterilized, and the penetration of the electron beam and the X-rays into the accommodated object 42 is prevented. Further, the container 44 also has a function of maintaining sterility inside. Therefore, a space inside the container 44 is maintained in the sterile state. Note that as the container 44, for example, a petri dish is assumed, and a material containing lead or the like is used for a shielding material 44a. In addition, as the accommodated object 42, for example, a cell is considered.

Note that the container 44 illustrated in (c) of FIG. 2 has a shape in which a side wall of the upper container 44 covers the outside of a side wall of the lower container 44 at a side surface portion A thereof. In this way, when the upper and lower side walls partially overlap, since the X-rays are reflected and attenuated in gaps between the side walls, it is possible to accurately shield the X-rays even if there are gaps in the side walls. When more attenuation is required, the X-rays can be accurately shielded by adding a structure that partially bends a path of the gap.

Although the preferred embodiment of the present invention has been described above, the present invention is not limited thereto, and various modifications can be made without departing from the object of the present invention, such as, for example, in the above-described embodiment, the description was given as an example applied to the pass box, but it can also be applied to a glove box or an isolator, or a continuous sterilization system as disclosed in Patent Literature 1, and the like.

The invention claimed is:

1. A bacteria treatment mechanism comprising:
   a bacteria treatment unit having a space for performing bacteria treatment;
   a radiation irradiation unit that irradiates the bacteria treatment unit with radiation for performing the bacteria treatment;
   an air supply duct that supplies air to the bacteria treatment unit;
   a decontamination treatment fluid supply unit that supplies a decontamination treatment fluid to the air supply duct during initial decontamination of the air supply duct;
   an air filter that is provided between the decontamination treatment fluid supply unit and the bacteria treatment unit in the air supply duct and removes at least one of dirt and dust in a fluid passing through the air supply duct;

an air supply fan that is provided at an air supply port of the air supply duct and supplies air to the bacteria treatment unit via the decontamination treatment fluid supply unit and the air filter in the air supply duct; and an exhaust duct that exhausts molecules in the bacteria treatment unit, wherein the air supply duct, the bacteria treatment unit and the exhaust duct are connected so that the decontamination treatment fluid flows in an order of the air supply duct, the bacteria treatment unit and the exhaust duct by an air supply from the air supply fan.

2. The bacteria treatment mechanism according to claim 1, wherein the decontamination treatment fluid is a gas or mist having a decontamination function.

3. The bacteria treatment mechanism according to claim 2, wherein the decontamination treatment fluid contains hydrogen peroxide.

4. The bacteria treatment mechanism according to claim 1, wherein in the bacteria treatment unit, an object is sterilized by the radiation emitted from the radiation irradiation unit.

5. The bacteria treatment mechanism according to claim 4, wherein the object is a housing that accommodates an accommodated object therein and is formed of a shielding material that shields the radiation and secondary radiation that has a higher transparency than the radiation and is secondarily generated by the radiation, an exterior of the housing is sterilized by the radiation, and the radiation and the secondary radiation do not penetrate through the accommodated object.

6. The bacteria treatment mechanism according to claim 4, wherein the object is configured to wrap an accommodated object covered with a shielding material that shields the radiation and secondary radiation that has a higher transparency than the radiation and is secondarily generated by the radiation, with a sterile maintaining material that maintains the inside in a sterile state, an exterior of the sterile maintaining material is sterilized by the radiation, and the radiation and the secondary radiation do not penetrate through the accommodated object.

7. The bacteria treatment mechanism according to claim 4, wherein the object is a container that accommodates an accommodated object therein and is formed by providing a layer made of a shielding material that shields the radiation and secondary radiation that has a higher transparency than the radiation and is secondarily generated by the radiation inside a structure, an exterior of the container is sterilized by the radiation, and the radiation and the secondary radiation do not penetrate through the accommodated object.

8. The bacteria treatment mechanism according to claim 5, wherein the radiation is an electron beam and the secondary radiation is an X-ray.

9. The bacteria treatment mechanism according to claim 1, wherein a catalyst that decomposes molecules exhausted from the exhaust duct is provided.

10. The bacteria treatment mechanism according to claim 9, wherein the catalyst includes one of a first catalyst that decomposes hydrogen peroxide and a second catalyst that decomposes ozone.

11. The bacteria treatment mechanism according to claim 10, wherein an exhaust switching mechanism that guides the molecules exhausted to the exhaust duct to either the first catalyst or the second catalyst is provided.

12. The bacteria treatment mechanism according to claim 9, wherein the catalyst decomposes both hydrogen peroxide and ozone.

13. The bacteria treatment mechanism according to claim 1, wherein the bacteria treatment unit is a pass box.

14. A bacteria treatment method comprising:

an initial decontamination process of supplying a decontamination treatment fluid generated by a decontamination treatment fluid supply unit to an air supply duct via an air filter that is provided between the decontamination treatment fluid supply unit and a bacteria treatment unit in the air supply duct and removes at least one of the dirt and dust in a fluid passing through the air supply duct during initial decontamination of the air supply duct;

an initial air supply process of supplying air to the bacteria treatment unit via the decontamination treatment fluid supply unit and the air filter in the air supply duct by an air supply fan that is provided at an air supply port of the air supply duct;

an initial decomposition process of decomposing a fluid containing the decontamination treatment fluid exhausted from the bacteria treatment unit with a catalyst and releasing the fluid to the outside air;

a bacteria treatment process of irradiating the bacteria treatment unit with radiation to perform bacteria treatment of an object;

an aeration process of supplying air to the bacteria treatment unit through the air supply duct after the bacteria treatment, and exhausting the fluid in the bacteria treatment unit;

a decomposition process of decomposing the fluid in the bacteria treatment unit exhausted from the bacteria treatment unit with the catalyst or another catalyst and releasing the fluid to the outside air; and a take-out process of taking-out the object from the bacteria treatment unit after the decomposition process, wherein the decontamination treatment fluid flows in an order of the air supply duct, the bacteria treatment unit and an exhaust duct that exhausts molecules in the bacteria treatment unit by an air supply from the air supply fan.

15. The bacteria treatment mechanism according to claim 6, wherein the radiation is an electron beam and the secondary radiation is an X-ray.

16. The bacteria treatment mechanism according to claim 7, wherein the radiation is an electron beam and the secondary radiation is an X-ray.

* * * * *